(12) United States Patent
Tricca et al.

(10) Patent No.: US 6,790,035 B2
(45) Date of Patent: Sep. 14, 2004

(54) METHOD AND KITS FOR FORMING PONTICS IN POLYMERIC SHELL ALIGNERS

(75) Inventors: Robert E. Tricca, Danville, CA (US); Eric Kuo, Foster City, CA (US); Peter G. Knopp, Palo Alto, CA (US); Choi Woncheol, San Jose, CA (US); Craig R. Bruns, Danville, CA (US)

(73) Assignee: Align Technology, Inc., Santa Clara, CA (US)

( * ) Notice: Subject to any disclaimer, the term of this patent is extended or adjusted under 35 U.S.C. 154(b) by 230 days.

(21) Appl. No.: 09/967,822

(22) Filed: Sep. 28, 2001

(65) Prior Publication Data

US 2002/0081546 A1 Jun. 27, 2002

Related U.S. Application Data

(63) Continuation-in-part of application No. 09/313,289, filed on May 3, 1999, now Pat. No. 6,318,994.

(51) Int. Cl.[7] .............................................. A61C 3/00
(52) U.S. Cl. ............................. 433/6; 433/167; 264/19
(58) Field of Search ........................ 433/6, 167, 168.1, 433/171, 34, 202.1; 264/19, 20

(56) References Cited

U.S. PATENT DOCUMENTS

| | | | |
|---|---|---|---|
| 3,660,900 A | 5/1972 | Andrews | |
| 3,860,803 A | 1/1975 | Levine | |
| 4,080,736 A | * 3/1978 | Kennedy | ................. 433/36 |
| 4,504,225 A | 3/1985 | Yoshii | |
| 4,505,673 A | 3/1985 | Yoshii | |
| 4,676,745 A | * 6/1987 | Zurita | .................... 433/6 |
| 4,755,139 A | 7/1988 | Abbatte et al. | |
| 4,798,534 A | 1/1989 | Breads | |
| 4,856,991 A | 8/1989 | Breads et al. | |

(List continued on next page.)

FOREIGN PATENT DOCUMENTS

| | | |
|---|---|---|
| FR | 2 369 828 | 6/1978 |
| WO | WO 94/10935 | 5/1994 |

OTHER PUBLICATIONS

Wrune et al., "Physical and mechanical Properties of elastomers in orthodontic positioners," Am. J. thod. Dentofac. Orthop. 1989, 95:388–400.

Wells, "Application of the positioner appliance in orthodontic treatment," Am. J. Orthodont. 1970, 58:351–366.

(List continued on next page.)

*Primary Examiner*—John J. Wilson
(74) *Attorney, Agent, or Firm*—Townsend and Townsend and Crew LLP; Bao Tran, Esq.

(57) ABSTRACT

Systems and methods are disclosed for forming a pontic in a polymeric shell dental appliance, including providing a polymeric shell dental appliance of the type which is removably placeable over a patient's dentition, said shell having a concave trough which conforms to the teeth when the appliance is placed over the dentition and a location in the trough corresponding to a missing tooth; and depositing a flexible, durably affixed material in the location to form the pontic.

22 Claims, 6 Drawing Sheets

U.S. PATENT DOCUMENTS

| | | | |
|---|---|---|---|
| 4,936,862 | A | 6/1990 | Walker et al. |
| 5,011,405 | A | 4/1991 | Lemchen |
| 5,017,133 | A | 5/1991 | Miura |
| 5,035,613 | A | 7/1991 | Breads et al. |
| 5,055,039 | A | 10/1991 | Abbatte et al. |
| 5,059,118 | A | 10/1991 | Breads et al. |
| 5,139,419 | A | 8/1992 | Andreiko et al. |
| 5,186,623 | A | 2/1993 | Breads et al. |
| 5,273,429 | A | 12/1993 | Rekow |
| 5,338,198 | A | 8/1994 | Wu et al. |
| 5,340,309 | A | 8/1994 | Robertson |
| 5,342,202 | A | 8/1994 | Deshayes |
| 5,368,478 | A | 11/1994 | Andreiko et al. |
| 5,382,164 | A | 1/1995 | Stern |
| 5,395,238 | A | 3/1995 | Andreiko et al. |
| 5,431,562 | A | 7/1995 | Andreiko et al. |
| 5,447,432 | A | 9/1995 | Andreiko et al. |
| 5,452,219 | A | 9/1995 | Dehoff et al. |
| 5,454,717 | A | 10/1995 | Andreiko et al. |
| 5,456,600 | A | 10/1995 | Andreiko et al. |
| 5,474,448 | A | 12/1995 | Andreiko et al. |
| 5,528,735 | A | 6/1996 | Strasnick et al. |
| 5,533,895 | A | 7/1996 | Andreiko et al. |
| 5,536,169 | A * | 7/1996 | Yousefian ................. 433/6 |
| 5,542,842 | A | 8/1996 | Andreiko et al. |
| 5,549,476 | A | 8/1996 | Stern |
| 5,562,448 | A * | 10/1996 | Mushabac ................. 433/215 |
| 5,587,912 | A | 12/1996 | Andersson et al. |
| 5,605,459 | A | 2/1997 | Kuroda et al. |
| 5,607,305 | A | 3/1997 | Andersson et al. |
| 5,645,421 | A | 7/1997 | Slootsky |
| 5,975,893 | A * | 11/1999 | Chishti et al. ............. 433/6 |
| 5,984,682 | A * | 11/1999 | Carlson ..................... 433/180 |
| 6,334,773 | B1 | 1/2002 | Ahlen et al. |
| 6,572,372 | B1 * | 6/2003 | Phan et al. ................ 433/6 |

OTHER PUBLICATIONS

Kamada et al., "Case reports on tooth positioners with LTV vinyl silicone rubber and some case reports," J. Nihon University School of Dentistry 1982, 24(1):1–27.

Kamada et al., "Construction of Tooth Positioners with LTV Vinyl Silicone Rubber and Some Case Reports," J. Nihon University School of Dentistry Mar. 1982, 24(1):1–26.

Kesling, "The philosophy of the tooth positioning appliance," Am. J. Orthod. Oral. Surg. 1945, 31(6):297–304.

Kleeman et al., "The speed positioner," J. Clin. Orthod. 1996, 30:673–680.

Kuroda et al., "Three–dimensional dental cast analyzing system using laser scanning," Am. J. Orthod. Dentofac. Orthop. 1996, 110:365–369.

Nippon Dental Review, "New orthodontic device–dynamic positioner (D.P.)–1 Approach to the proposal of D.P. and transparent silicone rubber," 1980, 452:61–74.

Nippon Dental Review, "New orthodontic device–dynamic positioner (D.P.)–II, Practice application and construction of D.P. and transparent silicone rubber," 1980, 454:107–130.

Nippon Dental Review, "New orthodontic device–dynamic positioner (D.P.)–III, Case reports of reversed occlusion," 457:146–164.

Nippin Dental Review, "New orthodontic device–dynamic positioner (D.P.)–Case reports of reversed occlusion," 1980, 458:112–129.

Nishiyama et al., "A new construction of tooth repositioner by LTV vinyl silicon rubber," J. Nihon Univ. School of Dentistry 1977, 19(2):93–102.

Proffit et al., "The First Stage of Comprehensive Treament:Alignment and Leveling," Contemporary Orthodontics, Chaper 15, 470–533.

Raintree Essix & ARS Materials, Inc., Raintree Essix, Technical Magazine Table of contents and essix Appliances, http://www.Essix.com/magazine/dafault.html Aug. 13, 1997, 7 pages.

Schroeder et al., "Algoritms I," The Visualization Toolkit chapter 6–9.9, 1996.

Shilliday, "Minimizing finishing problems with the mini–positioner," Am. J. Orthod. 1971, 59:596–599.

Warunek et al., "Clinical Use of Silicone Elastomer Appliances," JCO Oct. 1989, 694–700.

Andrews, Lawrence F., D.D.S., "Straight Wire, The Concept and Appliance," The Six Keys to Optimal Occlusion, 15–24.

Andrews, Lawrence F., D.D.S., "The six steps to normal occlusion," Am. J. Orthod. Sep. 1972, 296–308.

Biostar Operation & Training Manual, Great Lakes Orthodontics, Ltd. 199 Fire Tower Drive, Tonawanda, New York, 14150–5890, 20 pages.

Chiappone, "Constructing the gnathologic setup and positioner," J. Clin. Orthod., 1980, 14:121–133.

Cottingham, "Gnathologic clear plastic positioner," Am.J. Orthod. 1969, 55:23–31.

Cureton, "Correcting malaigned mandibular incisors with removable retainers," J. Clin. Orhtod. 1996. 30:390–395.

Elasser, "Some oobservations on the history and uses of the Kesling positioner," Am. J. Orthod. 1950, 36:368–374.

* cited by examiner

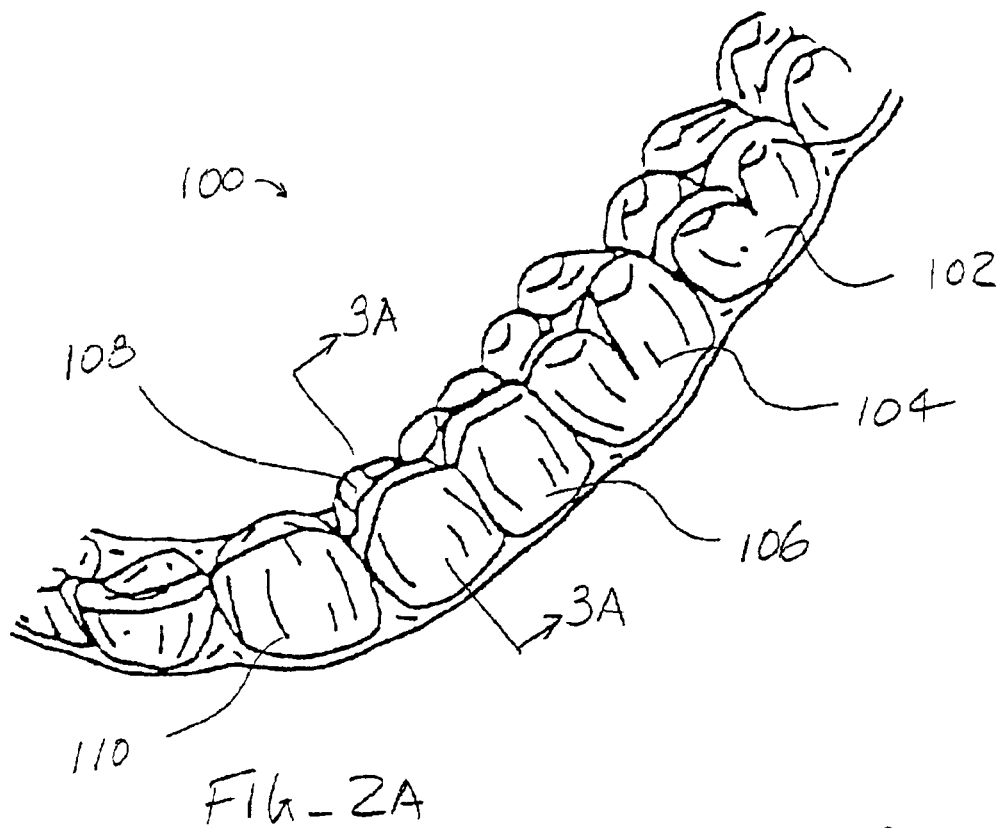
FIG_2A
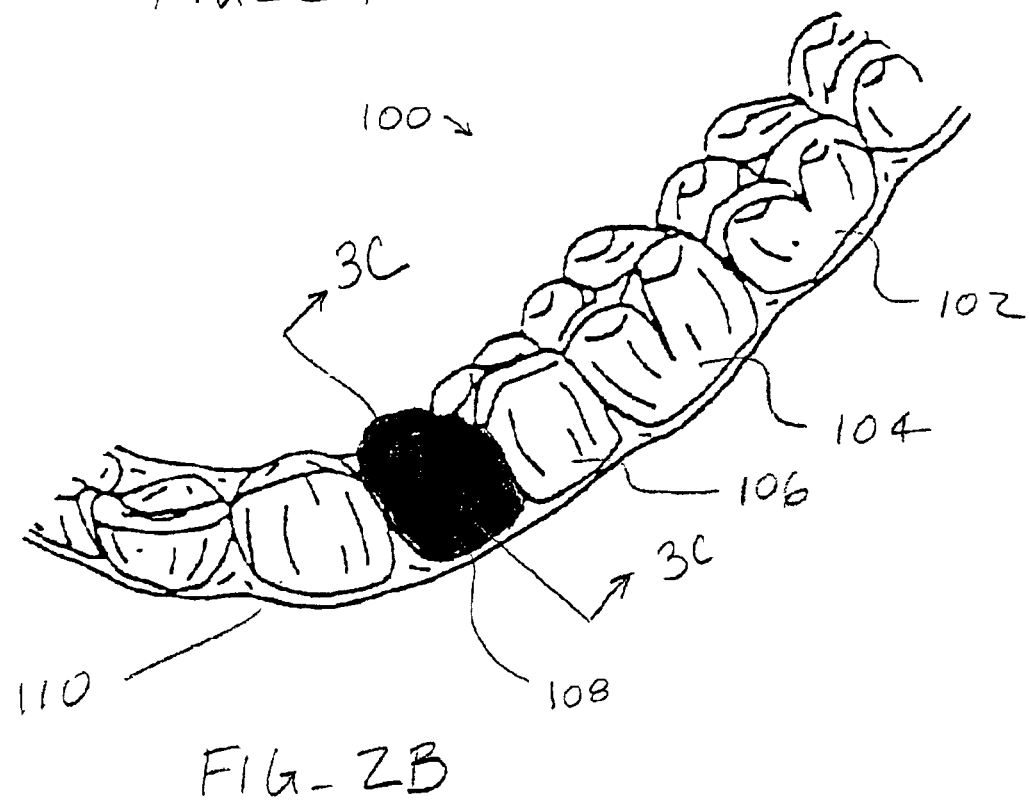
FIG_2B

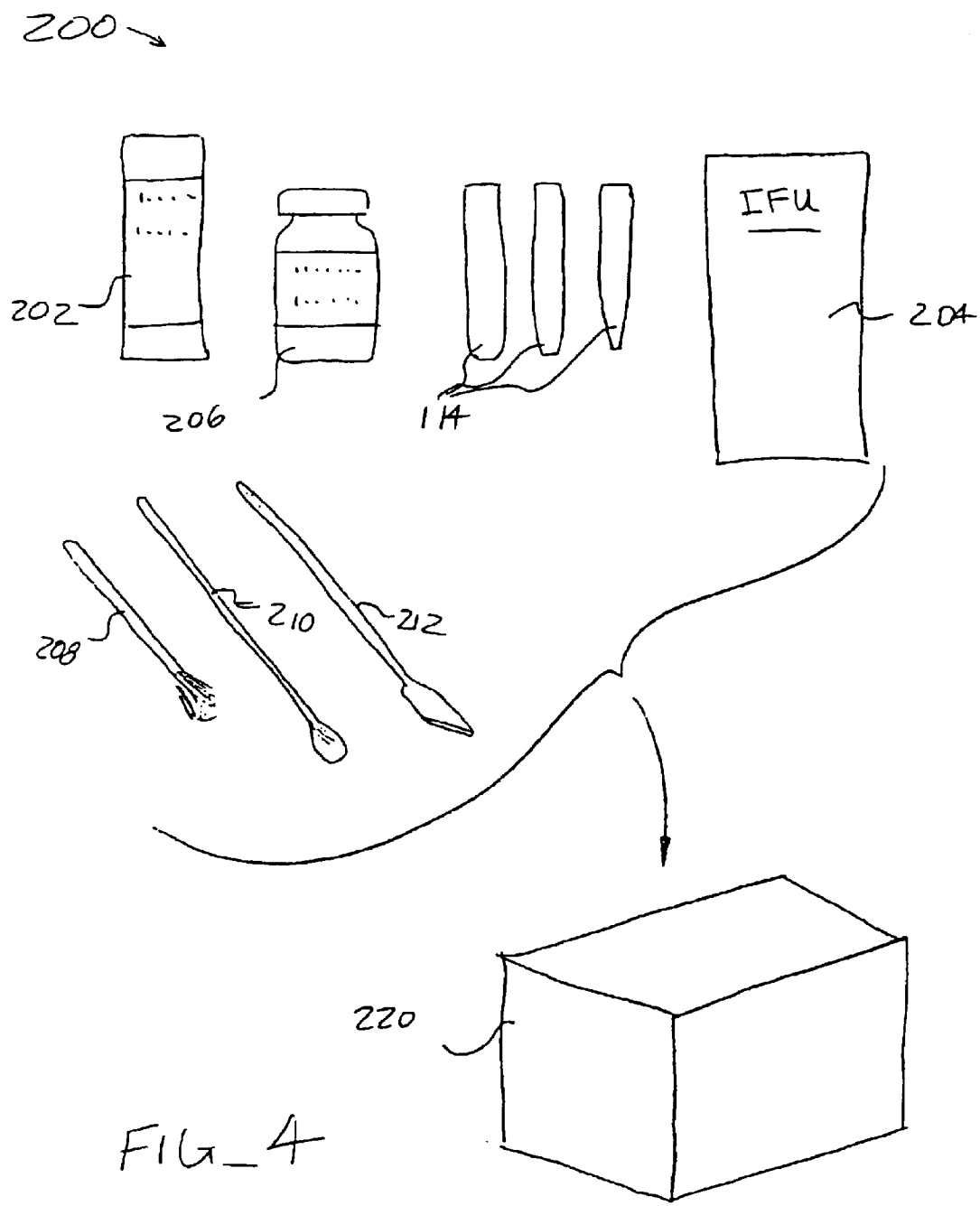
FIG_4

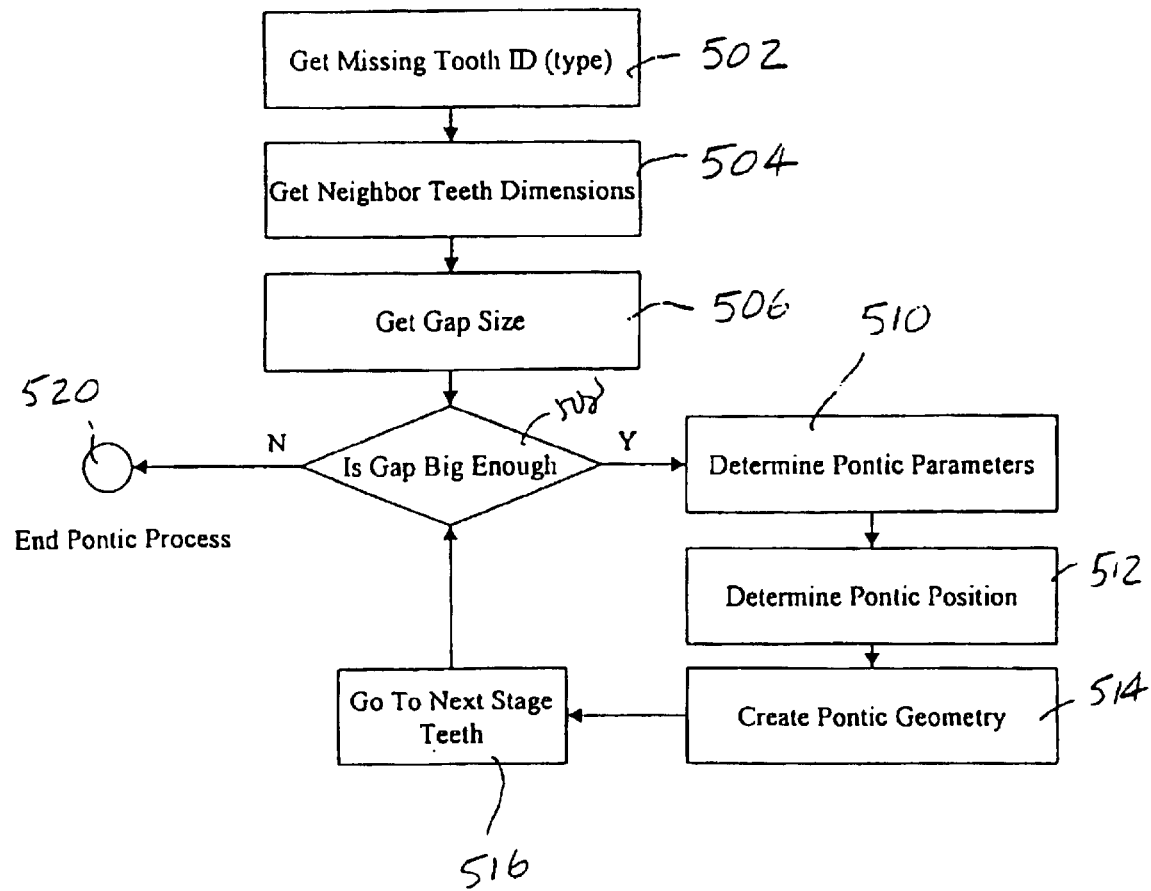
FIG_5

METHOD AND KITS FOR FORMING PONTICS IN POLYMERIC SHELL ALIGNERS

CROSS-REFERENCES TO RELATED APPLICATIONS

This application is related to a continuation-in-part (CIP) entitled Tooth Treatment Plan to prior application Ser. No. 09/313,289, filed May 13, 1999, now U.S. Pat. No. 6,318,994 and is related to prior application Ser. Nos. 09/169,036 and 09/169,034 both filed Oct. 8, 1998.

BACKGROUND OF THE INVENTION

1. Field of the Invention

This invention relates in general to orthodontics and more particularly to methods and kits for for providing pontics in orthodontic appliances.

2. Description of the Background Art

Orthodontic treatments involve repositioning misaligned teeth and improving bite configurations for improved cosmetic appearance and dental function. Repositioning teeth is accomplished by applying controlled forces to the teeth over an extended period of time. This is conventionally accomplished by wearing what are commonly referred to as "braces." Braces comprise a variety of appliances such as brackets, bands, archwires, ligatures, and O-rings. After they are bonded to the teeth, periodic meetings with the orthodontist are required to adjust the braces. This involves installing different archwires having different force-inducing properties or by replacing or tightening existing ligatures. Between meetings, the patient may be required to wear supplementary appliances, such as elastic bands or headgear, to supply additional or extraoral forces.

Although conventional braces are effective, they are often a tedious and time-consuming process requiring many visits to the orthodontist's office. Moreover, from a patient's perspective, they are unsightly and uncomfortable. Consequently, alternative orthodontic treatments have developed. A particularly promising approach relies on the use of elastic positioning appliances for realigning teeth. Such an appliance may be comprised of a thin shell of elastic material, referred to as an "aligner" that generally conforms to a patient's teeth but is slightly out of alignment with the initial tooth configuration. Placement of an aligner over the teeth applies controlled forces in specific locations to gradually move the teeth into the new configuration. Repetition of this process with successive appliances comprising new configurations eventually moves the teeth through a series of intermediate arrangements to a final desired arrangement. A full description of an exemplary elastic polymeric positioning appliance is described in U.S. Pat. No. 5,975,893, and in published PCT application WO 98/58596 which designates the United States and which is assigned to the assignee of the present invention. Both documents are incorporated by reference for all purposes.

Systems of preformed aligners employing technology described in U.S. Pat. No. 5,975,893, are commercially available from Align Technology, Inc., Santa Clara, Calif., under the tradename Invisalign® System. Align Technology, Inc., is the assignee of the present application. The Invisalign® System relies on designing and fabricating the aligners to be worn by the patient throughout treatment. The design of the aligners relies on computer modeling of a series of successive tooth arrangements, and the individual aligners are designed to be worn over the teeth and to reposition the teeth to each of said tooth arrangements. Usually, the set of aligners which is designed and fabricated at the outset of the treatment is able to successfully reposition the teeth to a final desired arrangement.

With the Invisalign® System, as well as with other conventional orthodontic treatment systems, it is sometimes necessary to extract one or more teeth prior to tooth repositioning. At present, the Invisalign® System does not provide for filling in the space or void which remains within the aligner after the tooth is extracted with a structural component such as an artificial tooth which is commonly referred to as a dental pontic.

The design and fabrication of dental pontics are described in U.S. Pat. Nos. 6,186,790; 6,050,820; 6,049,743 and 5,613,845, the full disclosures of which are incorporated herein by reference. Currently, dental professionals trained in the use of the Invisalign orthodontic system are using a variety of materials and techniques known in the art to fabricate dental pontics which can be worn in the aligner extraction site(s). The most commonly employed materials are tooth-shaded dental composites typically used to repair carious lesions or fabricate provisional (temporary) crowns and bridges. These materials consist mainly of a polymer matrix and dispersed reinforcing inorganic filler particles. Typical polymers used are based on dimethacrylate such as Bis-GMA or urethane dimethacrylate (UDMA). Quartz, lithium aluminum silicate and barium, strontium, or zinc glasses have been commercially distributed as fillers. Typically these materials are packaged as a two-paste (base/catalyst) system. The polymer matrix may be visible light curable, self-curing, dual curing, and vacuum, heat and pressure curable compositions as well as any combination thereof. A popular method for mixing and dispensing these materials involves the use of an automix system whereby a dispensing gun is utilized to dispense the base and catalyst, which are in separate cartridges, through a mixing cannula directly into the extraction site. Commercial examples of the autopolymerizing composites are Luxatemp Plus (DMG/Zenith), Integrity (Dentsply/Caulk), Protemp Garant (ESPE) and Turbo Temp (Danville Engineering). Alternatively light cured composites may be used to fabricate dental pontics. Commercial examples of light cured composites are Revolution (Kerr), Star-Flow (Danville Engineering), and Tetric (Vivadent). Other useful dental composite materials are based on the methyl methacrylate polymer. Such acrylic polymers are well known and commercially available for example as Jet Tooth Shade self-curing acrylic resin by Lang Dental.

Although dental composites have been used to fabricate dental pontics for the Invisalign system there remain two important disadvantages to using these materials. First the ability of these materials to bond to the aligner thermoplastic is poor and second these materials are very stiff and non-flexing. These characteristics significantly compromise retention of the pontic in the aligner especially if it is subjected to torsional or flexing forces such as when the aligner is either being inserted or removed from a patient's mouth or while the patient is cleaning their aligner using a cleaning device such a toothbrush or denture brush.

While it has been proposed to paint or color a portion of the aligner which overlies the void (see co-pending application Ser. No. 09/454,278, the full disclosure of which is incorporated herein by reference), partial coloring of the aligner can affect the light transmitting properties and be unaesthetic and the lack of any underlying structure can weaken or lessen the resilience of the aligner and limit its effectiveness.

For these reasons, it would be desirable to provide methods, systems, and kits for modifying an aligner to accommodate patients who have had teeth extracted prior to treatment with an aligner or other polymeric shell orthodontic appliance. It would be particularly desirable if the methods would permit an orthodontist or other clinician to modify an aligner or other orthodontic appliance in the professional office, rather than having the modification done at the time of fabrication or at an off-site location. It would be further desirable still if the aligner could be modified by the treating clinician, fitted with the patient, and further modified if necessary for patient comfort or other reasons. The resulting modified aligners or other orthodontic appliances should be esthetically pleasing, and preferably should mask the absence of an underlying tooth while the aligner or other appliance is worn. At least some of these objectives will be achieved by the inventions described hereinafter.

U.S. Pat. No. 5,975,893, and published PCT application WO98/58596, have been described above. Co-pending application Ser. No. 09/454,278, which has been published as WO99/028,228, relates to the fabrication of aligners which have been colored to cover a void left where teeth have been removed. The full disclosures of each of these patents and pending applications are incorporated herein by reference.

SUMMARY OF THE INVENTION

The present invention provides methods and kits for forming a pontic in a polymeric shell dental appliance, such as the Invisalign® System aligners described above. In addition, the present invention provides for methods of using such modified aligners for treating patients having gaps between adjacent teeth, where the gaps resulted from prior tooth extractions or other causes. In addition to the esthetic improvement, i.e., the voids or empty spaces between teeth will be generally invisible, it is believed that the pontics may reduce the tendency of teeth to collapse inward toward each other as the teeth are moved to close the gaps during the orthodontic treatment. In the case of the Invisalign® System, successive aligners which are used to treat an individual patient can each be separately modified, with the pontic placed in a gap between adjacent teeth being reduced in size as the treatment progresses and the gap is gradually closed.

According to a first aspect of the present invention, a method for forming a pontic in a polymeric shell dental appliance, such as an Invisalign® System aligner, comprises providing a polymeric shell dental appliance of the type which is removably placeable over a patient's dentition. The shell will have a concave trough or cavity which conforms to the teeth when the appliance is placed or worn over the dentition. When the polymeric shell is worn, the treating clinician can determine the location in the appliance trough where a tooth is missing. The treating clinician will usually note the location on the appliance and further determine the width and shape of the gap between the teeth. Optionally, in the case of the Invisalign® System aligners, the aligner will have been shaped or otherwise modified to indicate the location where the gap will occur. If not, the treating clinician can simply mark the aligner or take other appropriate steps to determine the location of the space within the trough.

After the space (or spaces) is determined, the pontic is formed by filling the spaces(s) within the trough with a material that resembles a tooth. While it would be possible to shape a cured material into the desired geometry to be placed within the appliance trough, it will be much more convenient to fill the location with a relatively viscous but flowable and flexible material which can fill and conform to the interior volume of the target location within the appliance trough. Optionally, an adhesive or other treating material will be coated on the target location prior to filling with the pontic material. The flowable pontic material will then be cured to form the final pontic. Optionally, the shape of the pontic can be modified using spatulas (while it is still workable) and/or knives (after it has cured). Preferably, the pontic will be shaped so that it fills substantially the entire gap between adjacent teeth and extends down to the gingiva, without intruding upon the gingiva when the aligner or other appliance is worn.

In a specific embodiment of the present invention, curable silicone compositions, especially the addition-curable silicone rubber compositions known in the art are employed to form an elastomeric, flexible polyvinylsiloxane (PVS) dental pontic. Typically these polyvinylsiloxane materials are formed from a two component curable silicone prepolymer system. A first component, which is referred to as a "Base Paste", typically contains a vinylorganopolysiloxane dispersion, an organo hydrogen-polysiloxane, inorganic fillers and other additives well known in the art. The second component of this two-part composition is referred to as a "Catalyst Paste" and typically consists of a second portion of the vinyl polysiloxanes, polymerization initiators, accelerators, cross-linking agents and other additives well known in the art. The base and catalyst may either be hand mixed and delivered to the appliance trough using a spatula or application syringe or a mixing device such as an automix cartridge commonly used for impression materials may be employed to combine the proper volumes of base and catalyst. The tip size of the nozzle can be selected to provide a desired ribbon of material to be delivered to the appliance trough. Preferably, the tip of the nozzle will be held beneath the surface of the PVS as it is being dispensed within the appliance trough. By providing applicators having different tip diameters, the size of the material ribbon and the pontic can be selected by the treating physician.

Another class of curable silicone rubbers useful in forming elastomeric dental pontics are the condensation reaction silicones. Condensation silicones are supplied as either a paste and liquid or as two pastes. Typically the base paste consists of a silicone polymer with terminal hydroxy groups and a filler and the catalyst paste consists of a cross-linking agent (organohydrogen siloxane) and an activator such as dibutyl-tin dilaurate. On mixing the two pastes react by a condensation reaction causing cross-linking. Typically the setting reaction produces a gas such as hydrogen or an alcohol.

Prior to delivering the curable silicone rubber, an adhesive is applied to the aligner segment corresponding to the site of the missing tooth to enhance the bond between the PVS pontic and aligner thermoplastic.

After sufficient material has been dispensed to form the pontic, the treating clinician may optionally shape or form the pontic as desired, typically using conventional shaping tools, such as spatulas. The material will then be cured. In the case of PVS, curing will typically occur after five to ten minutes at room temperature but anybody skilled in the art can vary the material composition to allow for curing times <60 seconds or as long as 24 hours. If it is desired to expedite curing, the PVS material may be gently warmed, e.g., held under a warm water stream. After curing, shaping or trimming of the pontic may be performed using a knife, abrasive instrument, or the like.

Non-toxic, inorganic iron oxide pigments may be incorporated in the PVS polymer to provide for a tooth-colored shade for the finished pontic. Optionally, a range of tooth-colored PVS resins may be provided in a kit allowing the clinician to select a color that best matches patient's teeth. In a second aspect of the present invention, kits are provided comprising components of the system useful for performing the methods described above. In particular, the basic kit would include a curable, toothshaded PVS resin material such as described above in combination with instructions for use setting forth a method for forming the pontic within the trough of an aligner or other thin polymeric appliance having a trough or cavity which is removebly placed over teeth. In particular, the instructions will set forth a first step of determining the location in the trough where a tooth is missing from the patient's dentition, and a second step comprising filling the location with the filler so that the material resembles a tooth when the location is filled.

Optionally, the kit may further include other components, such as an adhesive for coating an interior surface of the appliance trough at the location to be filled. When an adhesive is supplied, the kit will typically also include a brush, sprayer, or other applicator for applying the adhesive to the appliance trough. The kit may still further comprise one or more nozzles for use with a filler applicator for dispensing the curable filler material within the appliance trough. Typically, the filler applicator will be a dispensing gun capable of applying the PVS resin in a controlled manner through the nozzle which is attached to the gun. More typically, the kit will include two or more nozzles, where each nozzle will have a different tip diameter to dispense a different ribbon size of the filler to most efficiently fill target locations of differing sizes. Further optionally, the kit may include two or more cartridges or other containers of the curable filler material, where the materials have different properties, such as color. Still further optionally, the kit could include one or more coloring materials to permit the clinician to mix and color the filler material at the time of use. In addition, the kit may include one or more shaping tools which permit precise sizing and shaping of the pontic. For example, the kit may be provided with a spatula for sizing and shaping the material before it is cured. Alternatively or additionally, the kit may comprise a knife, grinder, or other tool for shaping and removing the filler material after it has cured. To facilitate the fabrication of dental pontics in a manufacturing setting, the curable tooth-colored silicone rubber catalyst- and base-paste may be supplied in foil bags and precisely dispensed from a Pentamix system eliminating either hand-mixing or dispensing with a hand held dispensing gun.

In a third aspect of the present invention, improved methods for repositioning teeth after extractions or impatience with substantial gaps between adjacent teeth are provided. The improvements are in methods for repositioning teeth which use polymeric shell appliances each of which have a trough for receiving and resiliently repositioning the teeth, e.g., as in the Invisalign® System commercially available from Align Technology, Inc., assignee of the present application. The polymeric shell appliances have different geometries and are worn successively by a patient to reposition the teeth in a number of stages. The improvement comprises providing at least some of the polymeric shell appliances, also referred to as aligners, which have pontics at a location within the appliance trough which will fill a gap between teeth when the appliance is worn. Usually, each appliance worn will have a pontic at the location of the gap, and the size of the pontic may be decreased as the treatment progresses and the width of the gap closes. In addition to the esthetic benefits described above, the provision of a pontic within the gap as the teeth are being closed is believed to provide therapeutic benefits as well. In particular, the presence of the pontic will reduce or eliminate the tendency of teeth which are being closed over a gap to tilt or incline into the gap. Thus, it is expected that teeth which are treated with the polymeric appliances to close such gaps will remain generally more upright as they are moved, thus reducing or eliminating the need to correct any tilt or inclination which is induced by the treatment.

BRIEF DESCRIPTION OF THE DRAWINGS

FIGS. 2A and 2B illustrate a portion of the aligner of FIG. 1 prior to placement of a pontic (FIG. 2A) and after placement of a pontic (FIG. 2B). For convenience, placement of the pontic is shown in black, but it will be appreciated that in practice the pontic will usually be a shade of white selected to match the patient's teeth.

FIG. 4 illustrates a kit constructed in accordance with the principles of the present invention.

FIG. 5 illustrates an exemplary process for generating an aligner capable of receiving the pontic material.

DESCRIPTION OF THE SPECIFIC EMBODIMENTS

Figure 1:
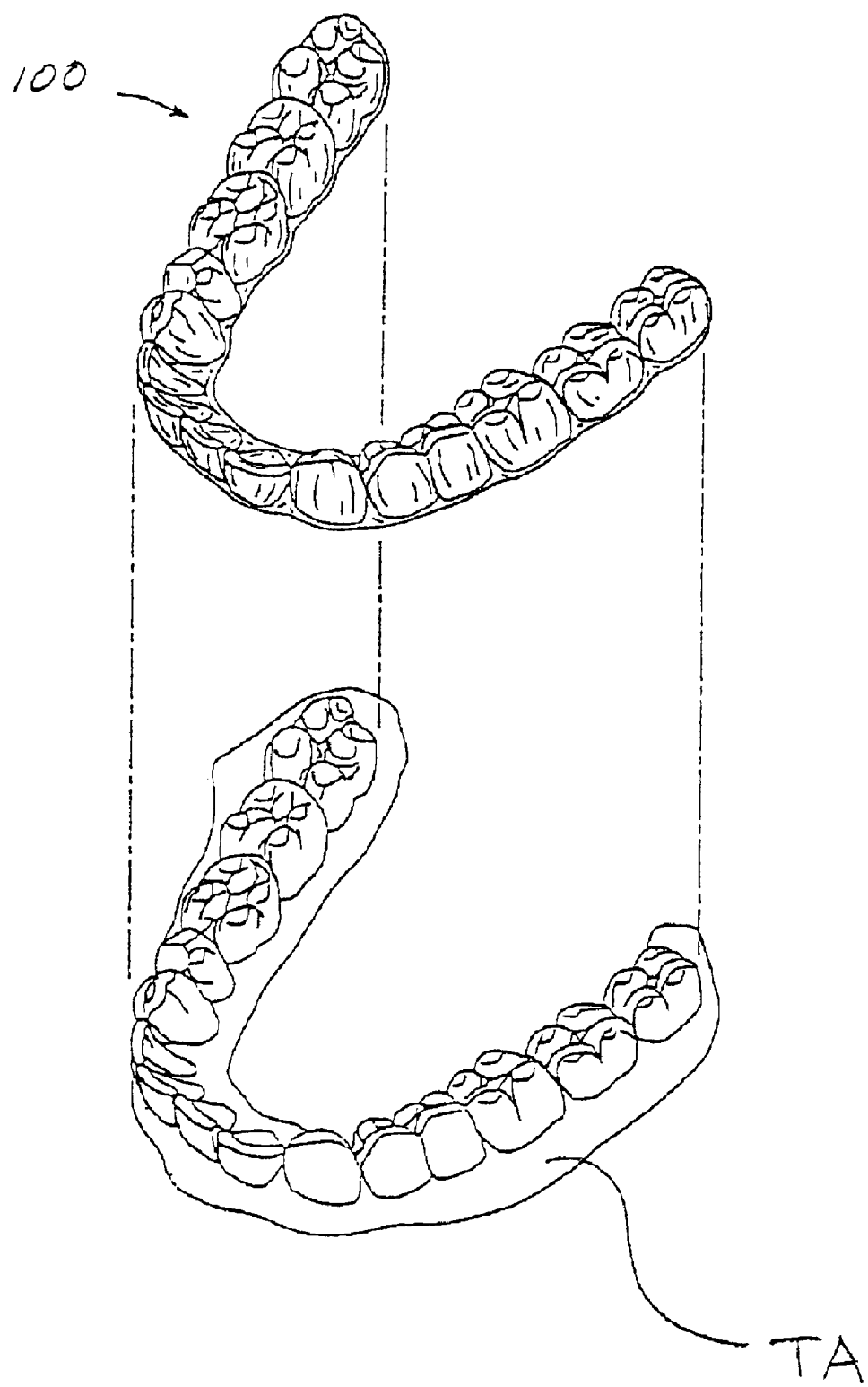
FIG. 1 illustrates an aligner of the type employed in the Invisalign® System being placed over a patient's teeth.

The present invention provides improved methods and kits for the use of aligners 100 for positioning teeth in a tooth arrangement TA, as illustrated in FIG. 1. The aligner is a thin shell polymeric appliance of the type commercially available as part of the Invisalign® System available from Align Technology, Inc., Santa Clara, Calif. The planning and fabrication of such aligners is described in detail in issued U.S. Pat. No. 5,975,893, the full disclosure of which has previously been incorporated herein by reference. The aligners 100 are worn by a patient over the tooth arrangement for a sufficient time to rearrange the teeth to a desired subsequent tooth arrangement. A plurality of successive aligners are worn until an entire course of the treatment is completed.

As shown in FIG. 2A, the aligner 100 will include a number of individual tooth-shaped segments 102, 104, 106, 108, and 110. Each of these individual segments will be designed to fit over an individual tooth, with the particular placement of the segment being moved slightly to effect a corresponding tooth movement while the aligner is worn.

For the purposes of describing the present invention, it will be assumed that the tooth corresponding to segment 108 will be extracted, e.g., to remove over-crowding. Once the tooth is removed, of course, there will be a void or gap left between the teeth which are beneath segments 106 and 110. The purpose of the present invention is to provide an artificial tooth, commonly referred to as a pontic, within the cavity or trough of the aligner 100 which would have covered the tooth prior to extraction. The aligner 100 having a pontic formed in the interior of segment 108 is illustrated in FIG. 2B. For ease of illustration, presence of the pontic is shown by coloring the segment 108 black. In actual practice, of course, the pontic will usually be colored a shade of white to match the patient's other teeth.

Figure 3A:
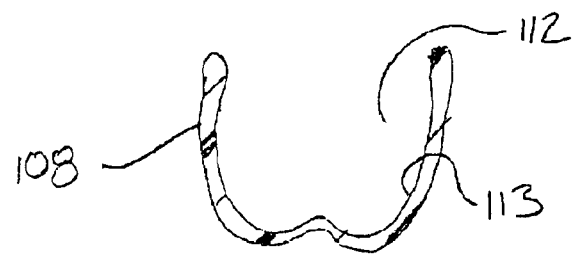
FIG. 3A is a cross-sectional view taken along line 3A—3A of FIG. 2A, showing a view of the aligner prior to filling with the pontic material.
Figure 3B:
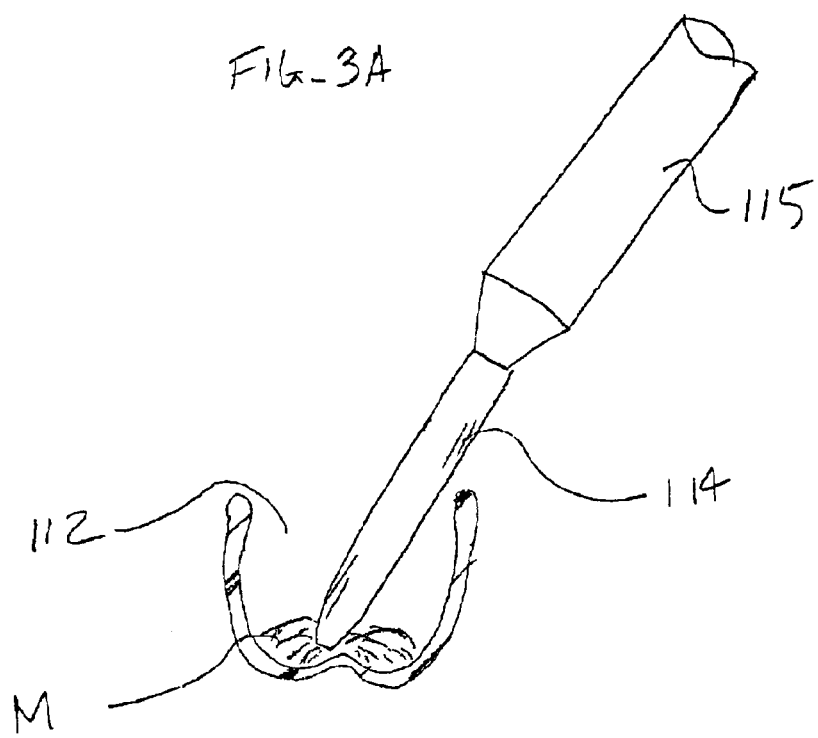
FIG. 3B illustrates filling of the aligner with the pontic material.
Figure 3C:
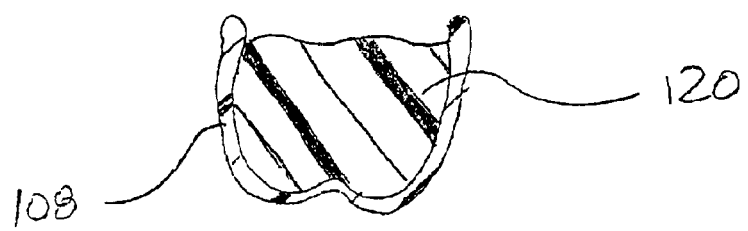
FIG. 3C is a cross-sectional view taken along line 3C–3C of FIG. 2B, showing the aligner after the pontic has been formed therein.

Referring now to FIGS. 3A–3C, formation of a pontic 120 in the tooth segment 108 of aligner 100 will be illustrated. Initially, the trough 112 of the tooth segment 108 is empty, as illustrated in FIG. 3A. A bonding agent is applied to the tooth aligner tooth trough as illustrated in FIG. 3B. The bonding agent may be a simple compound, more preferably a polymer which attaches or substantively, adhesively, cohesively or otherwise bonds the curable silicon rubber to the aligner thermoplastic. The preferred bonding agents can be those disclosed in German Pat. DE 19934117 to Engelbrecht et al. The pontic is preferably formed by dispensing a curable PVS prepolymer resin (M) as shown in FIG. 3B. Typically, the curable PVS prepolymer resin will be dispensed through a mixing nozzle 114 from an applicator 115. The applicator can be a conventional dispenser gun, e.g., holding a dual cartridge; one cartridge containing the uncured PVS resin base, inorganic fillers and other additives known in the art the other containing the catalyst components. As the trigger of the dispensing gun is squeezed, the PVS base and catalyst materials flow through the mixing nozzle where they are combined initiating the curing of the PVS rubber. The PVS rubber is dispensed through the mixing nozzle, where the width of the bead dispensed is determined by the tip diameter of the nozzle. Preferably, the tip diameter of the nozzle will be selected to provide an appropriate material bead size to fill the trough 112 at a desired rate. Useful tip diameters will be in the range from 0.01" inches to 0.2" inches, preferably from 0.03" inches to 0.10" inches. The PVS rubber will be dispensed, preferably while maintaining the nozzle tip beneath the surface of the material, until the trough 112 is substantially filled, as shown in FIG. 3C. At that point, the pontic 120 has been formed. Immediately after dispensing the PVS rubber in the aligner trough the user may, if necessary, sculpt and contour the material using a spatula or similar instrument. The user may continue to do this during the "working phase" of the resin curing process. Useful working phase times will be in the range from 30 seconds to 5 minutes, preferably from 45 seconds to 3 minutes. Curing or hardening of the PVS filler material will then take an additional 3 minutes to 10 minutes depending on the formulation. After the pontic material has cured, it may still be shaped using a knife, abrasive instrument, or the like. In addition to fitting the pontic so that it can be inserted and removed between the adjacent teeth, it is also desirable that the exposed portion of the pontic not intrude upon the gingiva. The treating clinician can place the aligner 100 over the patient's teeth to make sure that it fits properly before releasing the aligner to the patient.

Referring now to FIG. 4, a kit 200 adapted for forming pontics within aligners or other polymeric shell appliances will be described. The kit 200 will include at least a container 202 which holds the pontic material. Typically, the container 202 will be in the form of a cartridge which may be dispensed through a conventional applicator, such as a gun-type applicator used with the preferred PVS filler material. The kit 200 will also include instructions for use 204 which set forth the methods of the present invention, as generally described above. Optionally, the kit may further include one or more nozzles 114 which may be used together with the applicator, as generally described above. In preferred embodiments, the kits will include two or more nozzles, where the nozzles have different tip diameters to permit dispensing of different bead sizes of the filler material into the aligner. Further optionally, the kit may include a bonding agent, as described in German Patent DE 19934117 assigned to Engelbrecht et al. for coating the interior of the aligner prior to dispensing of the pontic material. When including the adhesive 206, a brush 208 may also be provided either separately or optionally within the cap of the adhesive container. Other tools, such as a spatula 210 for forming the filler material prior to hardening, a knife or other tool for forming the pontic material after hardening, and the like, may also be provided. Preferably, all components of the kit will be packaged together with a box, tray, pouch, tube, or other conventional medical device package 220.

FIG. 5 illustrates an exemplary process 500 for generating an aligner capable of receiving the pontic material. The process of FIG. 5 creates a pontic that is customized to each patient. The customization is needed since shapes of teeth vary: for the same tooth, different patients have different tooth sizes and shapes. In order to represent a generic tooth shape that can be modified for each patient, a standard parametric tooth model is employed, and the process 500 customizes the parametric tooth model to each patient.

Starting from the first tooth position that requires a pontic, the process 500 determines a tooth identification or tooth type (step 502). Next, the process 500 determines neighboring teeth dimensions (step 504). The parameters are determined by the neighboring teeth dimensions. The height of the pontic is determined in proportion to the neighboring teeth heights. The pontic thickness is also proportional to the neighboring teeth thickness. Other parameters can be predefined or proportional to the neighboring teeth.

The process 500 then determines the gap size based on the neighboring teeth dimensions as the pontic width also depends on the gap size (step 506). Next, the process 500 determines whether the gap provides sufficient clearance for the pontic (step 508). From step 508, if the gap is too small, the process exits (step 520). Alternatively, if the gap is sufficient, the process 500 determines the pontic parameters (step 510). It also determines the pontic position (step 512). The process 500 also creates pontic geometry for the current tooth (step 514). Step 514 completes the processing for the current tooth, and the next tooth for the current stage is selected (step 516) before the process loops back to step 508. The pontic is updated in each stage, thus each stage has a different pontic. Thus, the pontic will be updated as the stage changes.

Figure 6:
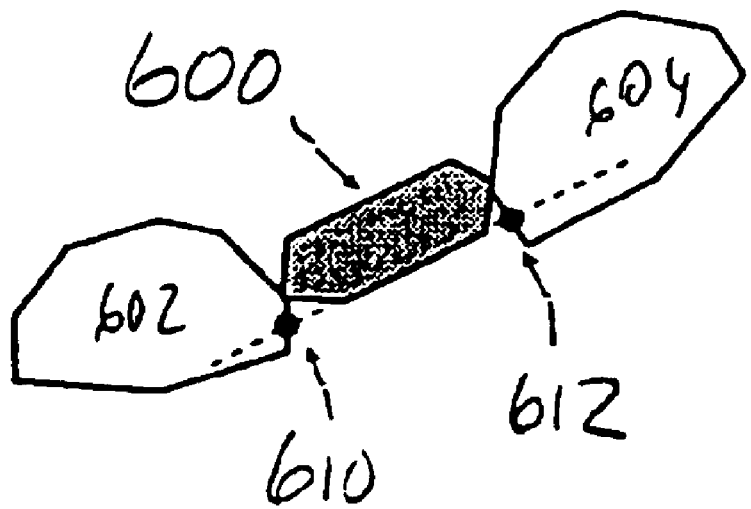
FIG. 6 shows an exemplary pontic in an aligner.

FIG. 6 shows an exemplary pontic 600 in an aligner. The position of the pontic 600 is determined by the neighboring teeth 602 and 604. As shown in FIG. 6, two points 610 and 612 on the interproximal area of the neighboring teeth are used to define an axis 620. The pontic 600 is placed in contact with a plane that passes the two points 610 and 612. The position can be manually adjusted by the user.

Figure 7:
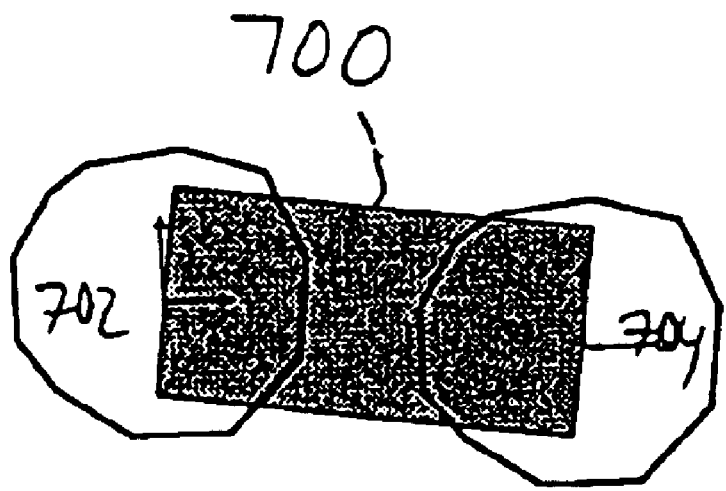
FIG. 7 shows an exemplary space filler in an aligner.

FIG. 7 shows an exemplary space filler 700 between two teeth 702 and 704 in an aligner. The space filler 700 is used when the missing tooth is in the posterior region of the jaw that is not likely to be visible. In such situation, a geometric beam is formed connecting the center of the teeth 702 and 704 and the beam width is selected that is smaller than the diameters of the teeth 702 and 704 and a geometric filling is performed to fill in the beam. The use of the space filler 700 provides structural strength to the resulting aligner while avoiding the costs associated with a pontic.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for forming a pontic in a polymeric shell dental appliance, said method comprising:
   providing a polymeric shell dental appliance of the type which is removably placeable over a patient's dentition, said shell having a concave trough which conforms to the teeth when the appliance is placed over the dentition;
   determining a location in the trough where a tooth is missing from the dentition;
   coating the trough with a bonding agent, and
   filling the location with a flowable material that resembles the tooth when the location is filled.

2. A method as in claim 1, wherein filling comprises dispensing a curable silicone rubber wherein the curable silicone rubber is an addition reaction polyvinylsiloxane.

3. A method as in claim 2, wherein the curable silicone rubber is tooth-shaded.

4. A method as in claim 3, further comprising selecting a curable silicone rubber a desired toothshade.

5. A method as in claim 1, wherein filling comprises dispensing a curable silicone rubber wherein the curable silicone rubber is a condensation reaction polysiloxane.

6. A method as in claim 1, wherein filling comprises dispensing a curable silicone rubber from a dispenser having a nozzle.

7. A method as in claim 6, wherein the nozzle is removable and dispensing comprises choosing a nozzle size and connecting the chosen nozzle to the dispenser.

8. A method as in claim 1, wherein filling comprises shaping the flowable material with a tool.

9. A method as in claim 1, wherein the material comprises a silicone rubber and filling comprises curing the silicon rubber to harden said material in situ.

10. A method for forming a pontic in a polymeric shell dental appliance, said method comprising:
    determining a location where a tooth is missing from a patient's dentition;
    generating a mold for a polymeric shell dental appliance with a cavity enclosing the location;
    forming a polymeric shell dental appliance of the type which is removably placeable over the dentition; and
    filling the cavity with a curable silicone rubber that resembles a tooth.

11. A method as in claim 10, wherein filling comprises dispensing a curable silicone rubber wherein the curable silicone rubber is an addition reaction polyvinylsiloxane.

12. A method as in claim 11, wherein the curable silicone rubber is tooth-shaded.

13. A method as in claim 10, wherein filling comprises dispensing a curable silicone rubber wherein the curable silicone rubber is a condensation reaction polysiloxane.

14. A method as in claim 13, further comprising selecting a curable silicone rubber source having a desired tooth-shade.

15. A method as in claim 10, further comprising filling in the cavity when generating the mold.

16. A method as in claim 10, further comprising filling in the cavity when the tooth is a posterior tooth.

17. A method for forming a pontic in a polymeric shell dental appliance, said method comprising:
    providing a polymeric shelf dental appliance of the type which is removably placeable over a patient's dentition, said shell having a concave trough which conforms to the teeth when the appliance is placed over the dentition and a location in the trough corresponding to a missing tooth;
    integrating a bonding agent into the material; and
    depositing a flexible, flowable material in the location to form the pontic.

18. The method of claim 17, wherein the bonding agent evaporates upon forming the pontic.

19. The method of claim 18, wherein the pontic has a range of flexibility depending on a solute in the solvent.

20. The method of claim 19, wherein a pontic is formed in the location between adjacent teeth.

21. The method of claim 17, wherein the bonding agent comprises a solvent.

22. A method for generating a polymeric shell dental appliance to cover a missing tooth, comprising:
    determining a tooth type for the missing tooth and neighboring teeth dimensions;
    determining a height of the pontic based on the neighboring teeth dimensions;
    determining a pontic width based on the neighboring teeth dimensions; and
    generating a polymeric shell dental appliance of the type which is removably placeable over a patient's dentition, said shell having a closed concave trough which conforms to the teeth when the appliance is placed over the dentition and a location in the trough having height and width dimensions corresponding to the missing tooth.

* * * * *

UNITED STATES PATENT AND TRADEMARK OFFICE
CERTIFICATE OF CORRECTION

| | | |
|---|---|---|
| PATENT NO. | : 6,790,035 B2 | Page 1 of 1 |
| APPLICATION NO. | : 09/967822 | |
| DATED | : September 14, 2004 | |
| INVENTOR(S) | : Tricca et al. | |

It is certified that error appears in the above-identified patent and that said Letters Patent is hereby corrected as shown below:

Please delete item (63) from the title page of the above-identified patent:

"Related U.S. Application Data

(63) Continuation-in-part of application No. 09/313/289, filed on May 3, 1999, now Pat. No. 6,318,994."

In the Specification

Please delete the "*Cross-Reference to Related Applications*" entry at column 1, lines 8-12.

Signed and Sealed this
Thirteenth Day of May, 2014

Michelle K. Lee
*Deputy Director of the United States Patent and Trademark Office*